United States Patent [19]
Anderson et al.

[11] Patent Number: 5,288,516
[45] Date of Patent: Feb. 22, 1994

[54] PROCESS OF PRODUCING BIOABSORBABLE FILAMENTS

[75] Inventors: Mary B. Anderson, Milford, Ohio; Paul D. Seemuth, Kinston, N.C.

[73] Assignee: E. I. Du Pont de Nemours and Company, Wilmington, Del.

[21] Appl. No.: 16,423

[22] Filed: Feb. 11, 1993

[51] Int. Cl.⁵ .............................. B05D 3/12
[52] U.S. Cl. .................... 427/171; 427/177
[58] Field of Search ................. 427/171, 177

[56] References Cited

U.S. PATENT DOCUMENTS

| | | | |
|---|---|---|---|
| 2,683,136 | 7/1954 | Higgins | 260/78.3 |
| 3,297,033 | 1/1967 | Schmitt et al. | 128/335.5 |
| 3,636,956 | 1/1972 | Schneider | 128/335.5 |
| 3,839,297 | 10/1974 | Wasserman et al. | 260/78.3 R |
| 3,954,635 | 5/1976 | Cummings et al. | 252/8.9 |
| 4,027,676 | 6/1977 | Mattei | 128/335.5 |
| 4,033,938 | 7/1977 | Augurt et al. | 260/78.3 R |
| 4,243,775 | 1/1981 | Rosensaft et al. | 67/4 |
| 4,300,565 | 11/1981 | Rosensaft et al. | 128/335.5 |
| 4,700,704 | 10/1987 | Jamiolkowski et al. | 128/335.5 |

*Primary Examiner*—Bernard Pianalto

[57] ABSTRACT

In the production of stretch Oriented poly(hydroxycarboxylic acid) filaments suitable for use in medical products (e.g. sutures), high speed production is achievable by application, prior to the drawing step, of a lubricant which minimizes filament breakage and facilitates the use of draw ratios of at least 2:1, more typically at least 5:1.

19 Claims, No Drawings

PROCESS OF PRODUCING BIOABSORBABLE FILAMENTS

BACKGROUND OF THE INVENTION

1. Field of the Invention

This invention relates to the production of polyhydroxy acid (PHA) filamentary products, particularly bioabsorbable products. An aspect of this invention relates to a process for making PHA filamentary products at high speed and with $\geq 2X$ stretch orientation (a draw ratio $\geq 2:1$). Still another aspect of this invention relates to a method for using lubricant for facilitating the stretch orientation of filaments.

2. Description of the Prior Art

Bioabsorbable filamentary products compatible with living tissue have been used for decades. For example, surgical wounds can be closed with the aid of such products (sutures, clamps, etc.). Over a period of time, the product gradually loses its physical strength as it becomes absorbed into the wound site, and it also seems to disappear because of its compatibility with or susceptibility to degradation by living tissue. However, enough physical strength is retained by the product to hold the wound closed until a considerable amount of healing has taken place.

Early on, bioabsorbable monofilament surgical products were developed from naturally-derived collagen materials (e.g. the so-called "catgut" sutures), and these collagen products are still in use today, but it has long been recognized that collagen products and particularly monofilament collagen products have certain inadequacies, such as nonuniformity and antigenic characteristics. "Poly(hydroxy acid)", i.e. poly(hydroxycarboxylic acid) or "PHA," monofilament and polyfilament (e.g. braided) surgical products have become welcome additions in the field of surgical products, due to their uniformity and predictability. (The PHA polymers are polyesters containing repeating hydroxycarboxylic acid units.) However, some of the essential mechanical properties of bioabsorbable PHA surgical products can only be obtained when the freshly-spun filaments are drawn (stretch-oriented). See U.S. Pat. No. 3,297,033 (Schmitt et al), issued Jan. 10, 1967 and U.S. Pat. No. 3,636,956 (Schneider), issued Jan. 25, 1972. For an early appreciation of stretch orientation of PHA fibers, see U.S. Pat. No. 2,683,136 (Higgins), issued Jul. 6, 1954.

The chemistry of the polymers that contain repeating hydroxycarboxylic acid units and that are suitable for the production of filaments or fibers is described in detail in U.S. Pat. Nos. 3,636,956, 3,839,297, 4,033,938, 4,243,775, 4,300,565, and 4,700,704.

For suture use, monofilaments were initially used. However, particularly in the case of PHA surgical products, it is generally conventional to spin a fine filament and then improve its handling characteristics, tensile strength, knotting strength, etc. by twisting together or braiding or otherwise combining several fine filaments into a multifilament structure, as in, for example, U.S. Pat. Nos. 3,297,033; 3,839,297 (Wasserman et al), issued Oct. 1, 1974; and 4,027,676 (Mattei), issued Jun. 7, 1977.

Although these synthetic sutures have excellent use properties, their production is relatively slow. For example, excessive breakage of the small denier individual filaments during the conventional processing steps of spinning, drawing to orient, annealing, and one or more wind-up steps can slow down production. Because of this breakage problem, the freshly-spun filaments are generally collected at relatively low speeds and then drawn in a separate step in which the drawn fiber is also collected at relatively low speeds (e.g. <100 m/min.), in some cases as slow as just a few meters per minute. See Example 8 of U.S. Pat. No. 4,300,565 (Rosensaft et al), issued Nov. 17, 1981, wherein the collection speed of the drawn filament is $5.2 \times 10$ feet/min or about 52 ft./min. Nevertheless, as indicated above, drawing or stretch orientation can be vital to the production of surgical products of good quality.

In the field of filament processing generally, processing finishes or lubricants have been used to minimize running tensions and filament-to-filament friction, reduce static buildup, prevent filament breaks due to running tension, etc. See U.S. Pat. No. 3,296,063 (Chandler), issued Jan. 3, 1967. Chandler's finishes do not appear to be hygroscopic, but other prior art finishes can pick up moisture (e.g. atmospheric moisture). The PHA filaments preferred for use in surgical structures are water-sensitive, and some are rather easily hydrolyzed, resulting in polymer degradation and loss of physical properties. Accordingly, finishes or lubricants for PHA filament processing must be carefully formulated to accommodate the peculiar problems of these polymers.

Various finishes have been used as coating materials on spun PHA filamentary products, typically prior or subsequent to processing these products into sutures, e.g. to improve handling properties, knot tying strength, etc. See U.S. Pat. No. 4,027,676, U.S. Pat. No. 3,954,635, and U.S. Pat. No. 3,297,033. U.S. Pat. No. 3,954,635 (Cummings et al) mentions the problem of flaws in the fiber which arise due to passage of the fiber through processing machinery (e.g. braiding apparatus). Typically, Cummings et al form the fiber into a yarn and then draw it at a ratio such as 4:1 and a temperature of 140° F. (60° C.) to obtain a yarn of, say, 50 denier.

SUMMARY OF THE INVENTION

It has been found that high speed production of PHA filamentary products, particularly bioabsorbable products, can be achieved while producing filaments useful in medical products such as sutures, vascular supports that can contain pharmaceutical agents, and patches. The high speed production (with minimal filament breakage) can be achieved, either in the context of a continuous spin-lubricate-draw-windup process or in the context of a process wherein the freshly spun filament is collected prior to stretch orientation, by the selection of a lubricant for the lubricating step which has an important combination of properties, including very low viscosity. It is not essential that this lubricant be removed before the filamentary material is made into medical products such as sutures. Thus, the lubricant or finish is:

1) biocompatible with mammals, particularly with humans;

2) sufficiently high in lubricity to minimize filament-to-filament friction and to protect against filament breakage during processing of freshly spun filaments, particularly during stretch orientation at draw ratios of at least 2X (preferably >5X);

3) liquid at processing temperatures, including normal ambient (room) temperature;

4) chemically and physically non-reactive with the filament composition (e.g. essentially free of water or moisture, including moisture picked up from the atmosphere);

5) hydrophobic; and 6) low in viscosity at the relevant temperatures (no more than about 100 cp, and preferably not more than about 10 cp, even at room temperature).

As indicated in the above description of the properties of the lubricant, the process of this invention can be carried out continuously (if desired) and at high overall speeds (>100 m/min., and, if desired,>1000 m/min at the drawn filament collection stage), at draw ratios >2:1, i.e.>2X (preferably>5X). One can avoid collecting the filamentary product prior to the drawing step or stage of the process; to maximize overall production speed, the drawing or stretch-orientation step preferably begins substantially immediately after the lubrication step.

DEFINITIONS

As used in this specification, the term "processing" means steps in the production of filamentary products starting with spun, un-drawn monofilaments. It includes the production steps and handling from the time the extruded filaments solidify through the final post-drawing wind up (drawn filament collection). This "processing", and particularly the drawing step, are the most severe handling steps and are often the major cause of filament breakage. It is breakage in the drawing step that typically dictates the maximum speed of production of oriented continuous filament bundles, and the prior art, maximum production speeds (drawn fiber collection speeds) have often been well below 100 m/min. and in some cases below 20 m/min. Subsequent to "processing", filaments made according to this invention can be subjected to any of the manipulations conventionally used to make medical products, e.g. twisting, braiding, cutting to lengths typically used for sutures, weaving, beaming, etc. Less preferably, products made by the process of this invention can be cut into staple fibers. Thus, the term "processing" as used herein does not relate to these steps subsequent to the wind-up of the initially produced oriented filaments.

As used herein, the term "non-reactive" means that the lubricant is chemically non-reactive with the filament polymer, and also is physically non-reactive in the sense of causing high friction or adhesion of filaments to filaments. To be non-reactive in this sense means that the lubricant is essentially free of water, even moisture picked up from the environment (e.g. from the atmosphere), due to the great sensitivity of preferred PHA filaments to water.

The term "lower", as in "lower aliphatic" denotes organic groups having from 1 to 6 carbon atoms, but chains and rings can be interrupted by hetero-atoms which take the place of carbon atoms. Thus, "higher" denotes groups having more than 6 carbon atoms.

DETAILED DESCRIPTION

A filament processing lubricant suitable for the process of this invention can be a composition comprising a plurality of substances, e.g. a composition comprising a mixture of two or more of the preferred chemical compounds described below. However, a single chemical compound can serve as the lubricant. Chemical compounds which are generally recognized as safe when in contact with the flesh or fluids (e.g. wound exudate) of mammals are preferred. Typically, suitable compounds are liquid hydrocarbons (e.g. $C_{10}$ to $C_{32}$ alkanes and unsaturated aliphatic compounds); poly(oxypropylene) compounds which are OH- or ether-terminated; partially or fully esterified polyols, including mono-, di-, or (preferably) tri-glycerides, mono-, di-, tri-, and tetra-esters of aliphatic polyols (e.g. triols other than glycerin and tetrols); esters of higher aliphatic carboxylic acids; and, preferably, low molecular weight silicone oils such as the poly(lower alkyl or di-lower alkyl)siloxanes. All of these classes of compounds have good lubricity, are chemically and physically non-reactive with the PHA of the filament, and are hydrophobic. When members of these classes of compounds are suitably selected, they are substantially non-toxic, are liquid at moderate processing temperatures (e.g. 15° to 100° C.), and are low in viscosity at moderately elevated processing temperatures and even at room temperature (20°-25° C.). For example, purified mineral oils, certain naturally-occurring saturated and unsaturated triglyceride oils (coconut oil, peanut oil, corn oil, etc.), certain stearic acid esters, and certain silicone oils are liquid at room temperature, low in viscosity, and reasonably safe for prolonged contact with surgical wounds of mammals. (They would therefore would not necessarily have to be cleansed from the surfaces of the filamentary material prior to use.)

The viscosity range of the lubricant is a matter of great importance, since, in this invention, lubricant viscosity seems to affect factors related to production efficiency or product quality, particularly draw ratios and drawing speeds. Even at room temperature (20°-25° C.), it is preferred that the viscosity of the lubricant be in the range of about 1 to about 100 cp, more preferably 1 to 10 cp. In the case of silicone oils such as the polydimethylsiloxanes, these very low viscosities are provided by polymers with molecular weights not exceeding about 4000, and a polydimethylsiloxane with, on average, only about 3 to 5 siloxane units and a molecular weight as low as 236 is available.

The lubricant is hydrophobic under processing and use conditions, so that the PHA will be well protected against hydrolytic degradations; such degradation can lead to loss of important physical properties of the filament. As indicated previously, the hydrophobic lubricant preferably attracts no water from the atmosphere (i.e. water vapor or moisture) which could by itself initiate some hydrolytic degradation, even under neutral or near-neutral conditions (lack of acidity or basicity).

The lubricant is preferably very low in equilibrium moisture content. Simple esters such as butyl stearate and triglyceride oils (e.g. corn oil) are less preferred for this reason, since these materials can contain 0.1%, or even as much as about 1%, by weight, of water. Even hydrocarbon oils can contain small amounts of moisture. Thus, low viscosity silicone oils are particularly preferred as lubricants due to their extremely low water content, which can be <100 parts per million (ppm), more typically <10 ppm, and can even be in the parts per billion range.

Moisture regain is a more significant problem than equilibrium moisture content. Any heating of the filament which occurs during processing can drive off the equilibrium moisture content of the lubricant, but lubricants which lack sufficient hydrophobicity can quickly reabsorb or readsorb atmospheric moisture. Lubricants which are sufficiently hydrophobic to act as a moisture barrier (e.g. toward atmospheric moisture) are preferred. The low viscosity silicone oils selected for use in this invention provide outstanding protection against moisture regain.

The synthetic polymers which come closest to (or exceed) the ability of collagen to be bioabsorbed are well known in the art and are the highly water-sensitive PHA's. These PHA's can be described as polyesters containing repeating hydroxy-(lower aliphatic carboxylic) acid units, preferably alpha-hydroxycarboxylic acid units (typically derived from cyclic dimers such as lactides, glycolides, and substituted 1,4-dioxane-2,5-diones) and omegahydroxycarboxylic acid (typically lactone-derived) units. These PHA's—especially those containing some poly(alphahydroxycarboxylic acid) units—can be hydrolyzed completely, even in near-neutral body fluids such as blood (pH=about 7.2) and in moist, moderately acidic (7>pH>4) biological environments. Thus, typical synthetic polymers useful in the process of this invention contain at least 15 % by weight of repeating units of the formula

where R is a straight or branched lower alkylene chain optionally interrupted by one or more hetero-atoms (e.g. —O—) and is preferably methylene or ethylene; m is 0 or I, R' is H or lower alkyl, R" is hydrogen or alkyl of up to about 22 carbons when m is 0 and H or lower alkyl when m is 1, R' and R" being the same or different. Preferably, R' is H, R" is lower alkyl, and m is zero, but a significant amountof repeating units can also be beta-hydroxy-lower aliphatic carboxylic acid units, gamma-hydroxy-lower aliphatic carboxylic acid units, and polylactones.

Selection of PHA's for use in this invention involves consideration of, among other things, the nature of the hydrolysis product formed when the PHA is broken down by the biological environment in which it is used. Hydroxycarboxylic acids such as glycolic and lactic acid are "familiar" to mammalian biological systems. These acids can be formed in the course of essential biological functions, e.g. as metabolites or the like, and hence can be dealt with rather easily by normal biological processes. The degree of water-sensitivity is a less important consideration. Thus, poly(caprolactone) is less water-sensitive as compared to poly(lactic acid) or poly(glycolic acid), but caprolactone and omega-hydroxyhexanoic acid are far less "familiar" to mammalian systems than $C_2$- and $C_3$-hydroxycarboxylic acids, hence the less biologically compatible nature of these $C_6$ hydrolysis products should be taken into account.

Accordingly, the most preferred filaments of this invention comprise polymers of polyglycolic acid or polylactic acid, including copolymers and polymeric blends containing major amounts of one or both of these. Specificity in optical isomerism of asymmetric monomers (e.g. lactide monomer) used to make these polymers is not of vital importance, and D-isomers or DL-racemates or other D- and L- mixtures are operative, the L(-) lactide being commercially preferred. Examples of other suitable polymers and filaments spun therefrom said to be useful as sutures are disclosed, for example, in U.S. Pat. No. 3,636,956 (Schneider), issued Jan. 25, 1972.

By use of the above-described lubricants, filaments melt spun from polymers such as polylactic acid and polyglycolic acid can readily be drawn and collected at production (windup) speeds of over 1500 meters per minute. In a continuous process, the speed at which the filaments emerge from the extruder or spinneret can be and preferably is much slower than the overall production speed, because the draw ratio increases this speed by a factor of at least 2, typically 2 to 20, so that the production speed is very high, yet breakage problems are minimized or eliminated by the effect of the lubricant, provided that the lubricant is properly applied (e.g. with a kiss roll) and is in the viscosity range described previously.

The melt spinning and drawing techniques used in this invention can also be conventional, except for the surprisingly high speeds made possible by a lubricant selected in accordance with principles of this invention. U.S. Pat. No. (Schneider) 3,636,956 at column 6 gives a good description of conventional aspects of the melt spinning and drawing of suture filaments from polylactide/polyglycolide polymers. Although a kiss roll is the preferred conventional means for applying the lubricant to the spun filament, other conventional means are known in the art, as explained below.

Typical of the production of filaments by the process of the present invention, molten polymer at a temperature of about 10° C. above the melting temperature is forced through a spinneret having a plurality of holes therein of much greater length than diameter. Filament spinning speeds from 40 to 1000 meters per minute can be used. The as-spun filaments are cooled and solidify.

The lubricant of the present invention is then applied to the individual filaments by any conventional means such as the kiss roll technique, i.e. bypassing the filament bundle over a roll wetted with lubricant, or by metered application bypassing the filaments over a lubricant feed hole that delivers a predetermined quantity of feed.

As noted previously, the as-spun filaments conventionally have been wound on a bobbin because drawing could not be carried out at the higher speeds of spinning, and this general type of intermediate collection of the filaments is optionally used in this invention also, but when the invention is practiced on a large commercial scale, a coupled continuous spin-lubricate-draw-windup ("in-line") system is preferred. Such continuous processes not only increase filament production speed, they also avoid the costly handling step of wind-up (collection) of the weak as-spun filaments and the need to feed these weak filaments to the drawing rolls at low speed. Continuous coupled processes also have the advantage of minimizing exposure of the filaments, particularly in their undrawn unoriented state, to degradation by humidity-induced hydrolysis.

After spinning and lubrication, the filaments are drawn between draw rolls, with the last draw roll having a surface speed sufficient to draw the filaments 2–20 times, and preferably 5–10 times the as-spun length (draw ratios of 2X to 20X, preferably 5X to 10X). Two or more draw rolls in series can be used, and a draw pin can be positioned between one or more sets of draw rolls to localize the filament stretching. Final drawing speeds (or speed of collection of drawn filaments) of 1500 meters per minute or more are achievable, preferably at least 1000 m/min. Prior to drawing of a plurality of filaments, the denier per filament is typically 2 to 100, but the denier per filament decreases substantially during the drawing step (e.g., "necking down" can occur). The drawn (stretch-oriented) filaments have a denier per filament of 1 to 30, more typically less than 10 dpf.

Following drawing, the filament bundle is preferably annealed at about 80°-120° C., normally for a few minutes, to stabilize the filaments in the drawn state.

The drawing step orients the polymer molecules and greatly increases the tensile strength. Strengths of at least 2 g/denier and preferably 7-10 g/denier are obtained. For a filament with a tensile strength of about 7 g/d, the preferred products have an elongation at break of less than 20%, an initial modulus of about 100 g/denier, and a toughness of about 0.6-1.2 g/denier. The filaments normally are in the range of 1.3-5 g/denier. The filament bundles can be twisted into a monofilament yarn or several filament bundles can be braided together to form a braided yarn of the desired total denier.

Numerous other techniques for preparing the filaments can be employed, so long as the spun filament is lubricated in accordance with this invention. By use of this step, filament separation from the bundle and resultant individual filament breakage with attendant production shut-down is greatly minimized. Most importantly the drawing speed can be increased to approach the speed of textile yarn production. Filament bundle speeds off the final draw roll of 1500 meters per minute and more are achievable, in contrast to the several yards per minute production speeds that are typical of prior processes.

While the invention has been described in terms of continuous filament products, the invention is also applicable to staple or cut fibers and yarns, fabrics and the like prepared from staple fibers. The staple fibers are prepared by conventional techniques of cutting continuous filaments into staple fibers, usually from ¼" or less to over 3" in length.

The following non-limiting Examples illustrate the principle and practice of this invention.

EXAMPLE 1

Polyglycolic acid polymer in granular from (molecular weight of 150000) is dried overnight in an oven at 80° C. This polymer is then fed through nitrogen to an extruder that is preheated to 115°-120° C. in the feed zone. The extruder contains a screw conveyor and is connected to a conventional pump, a sand filter pack and a spinneret having 17 holes of 9 mil diameter. The temperature along the screw, pump, filter pack and spinneret is 210°-240° C. The pump forces the molten polymer through the spinneret holes forming 17 filaments of about 30 denier per filament. The filaments fall from the spinneret through a vertical chamber in which the filaments are cooled and solidified. After solidifying, the filaments in the lower part of the chamber are coated, using a kiss roll, with polydimethylsiloxane of 5 cp viscosity. The filament bundle is then wound on a bobbin at the same rate as spinning to avoid draw orientation at this point.

The filament bundle is then drawn by feeding the undrawn bundle from the bobbin around an initial draw roll; then around a heated draw pin; then around an intermediate draw roll at 1245 meters per minute; then around a second heated draw pin; around a final draw roll; then to a heated annealing roll and to windup. The surface speed of the initial draw roll is 230 meters per minute, and the surface speed of the final draw roll is gradually increased to a speed of 1500-1700 meters per minute, giving a 6.5X draw. The final 6.5X drawn individual filaments are 2.0-2.5 denier.

When the final draw ratio is reached, the surface speed of the intermediate draw roll is 1245 meters/minute; the temperature of the first draw pin is 100° C.; and the temperature of the annealing roll is 100° C.

The filament bundles of 17 filaments are processed throughout the high speed drawing of this run with minimal filament separation from the bundle and minimal filament breakage. The final products of the run have strengths of 6 to 9 grams per denier and elongations at break of 30 to 32%.

Another run is made under essentially the same conditions except for draw roll speeds, and without the application of any lubricant to the filament bundle. The maximum obtainable final windup speed obtainable without filament breakage at a 6X draw ratio is 40 meters per minute.

EXAMPLE 2

Other composition filaments are processed in accordance with Example 1 using various lubricants meeting the criteria of the present invention, as shown in Table 1.

TABLE 1

| Run | Filament Polymer | Lubricant (Viscosity, 23° C.) | Draw Ratio |
|---|---|---|---|
| 2 | polylactide (50% l/50% d) | butyl stearate (10 cp) | 8X |
| 3 | polylactide (90% l/10% d) | erythritol, tetra-$C_8$-$C_{10}$ ester (59 cp) | 8X |
| 4 | polyglycolide/ polylactide (50/50) | glycerol, tri-$C_8$-$C_{10}$ ester (25 cp) | 10X |
| 5 | polyglycolide/ polylactide (80/20) | tridecyl stearate (28 cp) | 12X |
| 6 | polyglycolide/ polylactide (20/80) | trimethylol propane, tri-$C_8$-$C_{10}$ ester (34 cp) | 8X |
| 7 | polyglycolide | polydimethylsiloxane (2 cp) | 15X |
| 8 | polyglycolide | polydimethylsiloxane (5 cp) | 15X |
| 9 | polyglycolide | polydimethylsiloxane (10 cp) | 12X |
| 10 | polyglycolide | polydimethylsiloxane (20 cp) | 12X |
| 11 | polyglycolide | polydimethylsiloxane (90 cp) | 5X |
| 12 | polyglycolide | polydimethylsiloxane (120 cp) | 3X |

Excellent quality filament bundles (yarns) are produced at high speeds in accordance with the procedures set forth above except for Run No. 12 where the viscosity of the lubricant is found to be too high to perform effectively in high speed production.

EXAMPLE 3

Example was repeated, except that the step of winding up the lubricated filament on the bobbin was eliminated by arranging an "in-line" system in which the filaments, freshly coated with lubricant by the kiss roll were fed directly to the initial draw roll. The surface speed of the final draw roll and the heating temperature were the same as in Example 1. Separation of filaments from the filament bundle and filament breakage were not observed.

I claim:

1. In the process of preparing a stretch-oriented, bioabsorbable poly(hydroxycarboxylic acid) filament, the process comprising the steps of:

spinning a bioabsorbable poly(hydroxycarboxylic acid) into a filament to produce an as-spun filament, and drawing the as-spun filament to produce the stretch-oriented filament;

the improvement wherein:

the step of applying to the as-spun filament, prior to the drawing step, a lubricant that is biocompatible with mammals, has sufficient lubricity to minimize filament-to-filament friction and filament breakage, is liquid at the temperature of application, is hydrophobic, and has a viscosity at the temperature of application of about 1 to about 100 cp.

2. The process of claim 1 wherein the lubricant comprises a silicone oil having a molecular weight less than about 4000 and a viscosity at room temperature in the range of 1 to 100 cp.

3. The process of claim 1 wherein the poly(hydroxycarboxylic acid) comprises a polymer containing repeating units of the formula $$-C(R'R'')-CO-O-$$

where R' and R" are the same or different and are H or lower alkyl, at least one of R' and R" being H.

4. The process of claim 3 wherein R' and R" are each H in a major amount of the repeating units of the polymer.

5. The process of claim 3 wherein R' is H and R" is methyl in a major amount of the repeating units of the polymer.

6. The process of claim 1 wherein said as-spun filament is stretch oriented at a draw ratio ranging from about 2X to abut 20X.

7. The process of claim 1 wherein the stretch-oriented filament exits from the drawing step at a speed of at least 1000 meters per minute.

8. The process of claim 1 wherein the drawing step is carried out substantially immediately after the application of the lubricant to the as-spun filament.

9. The process of claim 8 wherein the lubricant has a viscosity at room temperature in the range 1–10 cp.

10. A process for the production of bioabsorbable poly(hydroxycarboxylic acid) filaments, comprising the steps of:

spinning bioabsorbable poly(hydroxycarboxylic acid) into a filament, without intermediate collection of the spun filament, applying a lubricant to the spun filament and stretch-orienting said filament at a draw ratio of at least 2X, said lubricant being a silicone oil; a liquid, lower aliphatic stearate ester; a liquid, lower aliphatic polyol ester of a $C_8$ to $C_{10}$ aliphatic carboxylic acid; or a mixture thereof, said lubricant having a room temperature viscosity in the range of about 1 to about 100 cp, and collecting the resulting stretch-oriented filament at a windup speed greater than 100 m/min.

11. The process of claim 10, wherein a said lubricant is a silicone oil or a silicone oil in admixture with a said stearate ester or a said polyol ester, and wherein the resulting stretch-oriented filament is collected at a windup speed greater than 1000 m/min.

12. The process of claim 10, wherein said draw ratio is at least about 5X.

13. The process of claim 10, wherein a said lubricant is a silicone oil having a room temperature viscosity of about 1 to about 10 cp.

14. The process of claim 10, wherein the denier of the spun and stretch-oriented filament does not exceed 30.

15. The process of claim 10, wherein a plurality of said filaments are spun and combined into a multifilament structure, and said multifilament structure is lubricated and stretch-oriented.

16. The process of claim 15, wherein the denier per filament of said multifilament structure does not exceed 30.

17. The process of claim 10 wherein said poly(hydroxycarboxylic acid) comprises a polymer containing repeating units of the formula $$-C(R'R'')-CO-O-$$

where R' and R" are the same or different and are H or lower alkyl and, at least one of R' and R" being H.

18. The process of claim 17 wherein (1) one of R' and R" is hydrogen and (2) the other is hydrogen or methyl.

19. The process of claim 10 wherein the poly(hydroxycarboxylic acid) is selected from the group consisting of (1) polyglycolic acid, (2) polylactic acid, (3) copolymers containing major amounts of one or both of glycolic acid and lactic acid, and (4) polymer blends containing major amounts of one or both of polyglycolic acid and polylactic acid.

* * * * *